United States Patent [19]

Gironda et al.

[11] Patent Number: 5,478,797
[45] Date of Patent: Dec. 26, 1995

[54] BROMATE STABILIZATION OF NITRATE-FREE 3-ISOTHIAZOLONES AT PH 4-5.1

[75] Inventors: Kevin F. Gironda, Alpha, N.J.; George H. Redlich, Norristown; Ramesh B. Petigara, Hatfield, both of Pa.

[73] Assignee: Rohm and Haas Company, Philadelphia, Pa.

[21] Appl. No.: 342,566

[22] Filed: Nov. 21, 1994

[51] Int. Cl.$^6$ ............................. A01N 25/22; A01N 43/80
[52] U.S. Cl. ........................... 504/156; 504/269; 514/372; 514/970; 71/DIG. 1
[58] Field of Search ...................................... 504/156, 269; 71/DIG. 1; 514/970, 372

[56] References Cited

U.S. PATENT DOCUMENTS

| | | | |
|---|---|---|---|
| 5,137,899 | 8/1992 | Petigara et al. | 504/156 |
| 5,145,501 | 9/1992 | Lashen et al. | 71/67 |

*Primary Examiner*—S. Mark Clardy
*Attorney, Agent, or Firm*—Michael B. Fein

[57] ABSTRACT

The present invention provides an improved method of stabilizing of 3-isothiazolone solutions using bromate compounds by buffering the pH of the solution in the range of 4 to 5.1, and compositions which comprise 3-isothiazolone compound, bromate compound stabilizer, and sufficient buffer to maintain the pH in said range.

10 Claims, No Drawings

BROMATE STABILIZATION OF NITRATE-FREE 3-ISOTHIAZOLONES AT PH 4-5.1

This invention relates to stabilization of 3-isothiazolones.

U.S. Pat. No. 5,145,501 of Sep. 8, 1992, discloses the use of bromate to stabilize from decomposition biocidally active 3-isothiazolone compounds in aqueous solutions which are free of metal nitrate salt. Such compositions have not achieved commercial success because the 3-isothiazolones which comprise the prevalent commercial products become brominated. We have discovered a solution to this problem by providing a method of stabilizing 3-isothiazolone compound in an aqueous solution which is free of nitrate and nitrite stabilizer compounds comprising A) introducing sufficient bromate compound to stabilize said 3-isothiazolone, and B) buffering the pH of said solution in a range of 4 to 5.1.

The 3-isothiazolones to which this invention is most applicable are 5-chloro-2-methyl-3-isothiazolone, 2-methyl-3-isothiazolone, and 2-n-octyl-3isothiazolone.

The invention is especially applicable to 5-chloro-2-methyl-3-isothiazolone and 2-methyl-3-isothiazolone, either individually or in admixture. When in admixture, the preferred ratio of chlorinated to unchlorinated 3-isothiazolone is from about 90:10 to 2:98 and especially preferred is a ratio of 3:1 to 4:1. Another mixture to which this invention is especially suitable for use in certain loci, such as latex or paint, comprises 2-methyl-3-isothiazolone and 2-n-octyl-3-isothiazolone The compositions of the invention are useful as biocides and comprise 3-isothiazolone compound, bromate compound present in an amount sufficient to stabilize said 3-isothiazolone against decomposition, solvent, and sufficient buffer to maintain the pH of said composition in a range of 4 to 5.1.

Preferred compositions comprise from about 0.5 to about 25% by weight of one or more of the isothiazolones and a stabilizing amount of a metal bromate salt in the range of from about 0.1 to about 15% by weight.

Solvents used to dissolve the isothiazolones may be water or a mixture of water and a water miscible organic solvent which dissolves the isothiazolones, are compatible with the proposed end use, do not destabilize the 3-isothiazolone, dissolve the metal bromate salt and do not react with the metal bromate salt to eliminate its stabilizing action. Suitable water miscible organic solvents are glycols, such as ethylene glycol, propylene glycol, diethylene glycol and dipropylene glycol. Water is the preferred solvent.

Any metal bromate salt can be used. The preferred metal bromates for this invention are lithium bromate, sodium bromate, potassium bromate, magnesium bromate, calcium bromate, strontium bromate, cobalt bromate, and zinc bromate. Especially preferred for use in this invention are lithium bromate, magnesium bromate, potassium bromate and sodium bromate. The amount of metal bromate used depends on the concentration of 3-isothiazolone. About 5–15% metal bromate is used to stabilize 5.1–25% concentrations of 3-isothiazolones, and about 0.1–5% to stabilize 0.5–5% concentrations.

Any buffer which maintains the desired pH is suitable. Preferred buffers are acetate/acetic acid, citrate/citric acid, formate/formic acid, and butyrate/butyric acid. Acetate/acetic acid is especially preferred.

The compositions of the invention are prepared by mixing the isothiazolone, bromate salt, solvent, and buffer in any order.

The term microbicide includes bactericides, fungicides, and algaecides. Microbicidal or biocidal activity is intended to include both the elimination of and inhibition of growth of microbial organisms, such as bacteria, fungi, and algae.

Uses of these stabilized microbicides are typically at any locus subject to contamination by bacteria, fungi, yeast or algae. Typically, loci are in aqueous systems such as cooling water systems, laundry rinse water, oil systems such as cutting oils, lubricants, oil fields and the like, where microorganisms need to be killed or where their growth needs to be controlled. However, these stabilized microbicides may also be used in all applications for which known microbicidal compositions are useful; preferred utilities of the compositions of the invention are to protect wood, latex, adhesive, glue, paper, textile, leather, plastics, cardboard, cosmetics, caulking, and feed.

Because isothiazolones are so active as microbicides and only low levels of metal bromate salts are required to achieve stabilization, the amount of metal bromate salts in systems being treated will be very low, and therefore it is not likely to interfere with other components in systems requiring protection or with systems to which protected systems will be applied.

It is known in the art that the performance of microbicides may be enhanced by combination with one or more other microbicides. Thus, other known microbicides may be combined advantageously with the composition of this invention.

In the following examples, samples were considered to pass when at least 75% of each of 5-chloro-2-methyl-3-isothiazolone and 2-methyl-3-isothiazolone in a mixture remained after 4 weeks storage at 55° C.

Example 1

The buffers used in the following examples were prepared as follows.

Sodium hydroxide and/or acetic acid were used for pH adjustments.

The buffer for pH 3 was prepared by adding 0.05 g. formic acid and 9.95 g. deionized ("DI") water to a 30 ml glass, screw cap vial and adjusting the pH to 3. The buffer for pH 4.5 was prepared by adding 0.07 g. acetic acid and 9.93 g. DI water to a 30 ml glass, screw cap vial and adjusting the pH to 4.5. The buffer for pH 6 was prepared by adding 0.15 g. potassium monobasic phosphate and 9.85 g. DI water to a 30 ml glass, screw cap vial and adjusting the pH to 6.

Example 2

Four samples were prepared, each in a 30 ml glass screw cap vial, by combining 0.025 g. (0.25%) sodium bromate, 9.815 g. of a buffer from Example 1, and 0.16 g. (1.5%) of a 3:1 weight ratio of 5-chloro-2-methyl-3-isothiazolone (CMI) and 2-methyl-3-isothiazolone (MI). Sample 2-1 was buffered at pH 3, Sample 2-2 at pH 4.5 and Sample 2-3 at pH 6. One sample did not receive any buffer. These samples were stored in an oven at 55° C. and analyzed for isothiazolone by HPLC with UV detection. The results follow.

| Sample | % MI/% CMI Remaining | | | |
|---|---|---|---|---|
| | 1 Week | 2 Week | 3 Week | 4 Week |
| unbuffered* | 85/99 | 70/95 | 61/95 | 48/91 |
| 2-1* | 65/84 | 53/86 | NA | NA |

-continued

| | % MI/% CMI Remaining | | | |
|---|---|---|---|---|
| Sample | 1 Week | 2 Week | 3 Week | 4 Week |
| 2-2 | 100/98 | 97/94 | NA | 97/78 |
| 2-3* | 97/83 | 78/82 | NA | 53/78 |

NA = not analyzed
* = comparative

These data show that only the sample with an initial pH of 4.5 passed after 4 weeks.

Example 3

An unbuffered sample (3-2) was prepared by combining 0.10 g. sodium bromate, 19.59 g. DI water, and 0.31 g. of a 3:1 ratio of CMI and MI in a 30 ml glass, screw cap vial. A pH buffered (pH 4.5) sample was prepared by combining 0.05 g. sodium bromate, 9.79 g. pH 4.5 buffer prepared according to Example 1, and 0.16 g. of a 3:1 ratio of CMI and MI. Both samples contain 0.5% sodium bromate and 1.5% 3-isothiazolone. Both samples were stored at 55° C. and analyzed by HPLC with UV detection at 1, 2, 3, and 4 weeks storage. Results are as follows:

| | % MI/% CMI Remaining | | | |
|---|---|---|---|---|
| Sample | 1 Week | 2 Week | 3 Week | 4 Week |
| 3-1 | 97/98 | 88/95 | 78/91 | 75/90 |
| 3-2* | 82/98 | 62/93 | 47/92 | 29/87 |

* = comparative

From these data it can be seen that the unbuffered sample failed by 2 weeks, while the pH buffered sample was stable for 4 weeks.

Example 4

Buffer was prepared in a 60 ml glass, screw cap vial by adding 0.21 g. acetic acid and 29.79 g. DI water. The solution was shaken and split into three 10 g. samples, each in a 30 ml glass, screw cap vial. The pH of the samples was adjusted to 4.0, 4.5, and 5.0 using sodium hydroxide and acetic acid. The pH 5.5 buffer was prepared by adding 0.14 g. acetic acid and 19.86 g. DI water and adjusting the pH to 5.5 with sodium hydroxide.

The isothiazolone used in this Example was a 3:1 ratio of CMI and MI.
Samples were prepared in 1 oz. glass vials as follows:
4-1. 0.05 g. sodium bromate, 9.79 g. pH 4.0 buffer, 0.16 g. isothiazolone.
4-2. 0.05 g. sodium bromate, 9.79 g. pH 4.5 buffer, 0.16 g. isothiazolone.
4-3. 0.05 g. sodium bromate, 9.79 g. pH 5.0 buffer, 0.16 g. isothiazolone.
4-4. 0.05 g. sodium bromate, 9.79 g. pH 5.5 buffer, 0.16 g. isothiazolone.
4-5. (comparative) 0.05 g. sodium bromate, 9.79 g. DI water, 0.16 g. isothiazolone All samples contain 0.5% sodium bromate and 1.5% isothiazolone. Sample 4-5 (comparative) contained no buffer. Samples were capped, shaken, pH measured and stored at 55° C. Analysis of the samples was performed after 1, 2, 3, and 4 weeks storage by HPLC with UV detection. The pH at each sampling point was also measured. These results are reported below.

| | % MI/% CMI Remaining | | | |
|---|---|---|---|---|
| Sample (pH) | 1 Week (pH) | 2 Week (pH) | 3 Week (pH) | 4 Week (pH) |
| 4-1 (4.04) | 91/96 (3.88) | 79/96 (3.83) | 67/91 (3.71) | 55/89 (4.01) |
| 4-2 (4.50) | 94/97 (4.41) | 91/96 (4.33) | 91/93 (4.33) | 76/88 (4.40) |
| 4-3 (5.10) | 97/93 (4.91) | 97/89 (4.74) | 94/83 (4.53) | 94/82 (4.74) |
| 4-4 (5.50) | 100/65 (4.26) | 97/63 (4.26) | NA | NA |
| 4-5 (3.68)* | 81/98 (2.77) | 63/96 (2.70) | 44/95 (2.57) | 28/91 |

NA = not analyzed
* = comparative

These data show that a pH of the samples must be at least 4 over the course of the 4 week period to maintain stability of the isothiazolones.

Example 5

Samples 4-1, 4-2, 4-3, and 4-5 from Example 4 were monitored for formation of brominated isothiazolones after 4 weeks. The results are reported in peak area of the chromatographic peak corresponding to the brominated isothiazolones. These numbers are not quantitative, but since the analytical amounts of each sample and all subsequent dilutions were the same, then peak areas are a relative measure of the amounts of brominated isothiazolones produced.

| Sample (pH) | Peak Area of Brominated Isothiazolone |
|---|---|
| 4-1 (4.04) | 52,114 |
| 4-2 (4.50) | 15,818 |
| 4-3 (5.10) | 0 |
| 4-5 (3.68)* | 94,965 |

* = comparative

These data show that buffering the sample between pH 4 and 5.1 greatly reduces the amount of brominated isothiazolones formed.

Example 6

The effect of buffering on the stabilizing ability of bromate at various concentrations was determined. The isothiazolone used in this Example was a 3:1 ratio of CMI and MI. Samples were prepared in 1 oz. glass vials as follows:
6-1. 0.20 g. sodium bromate, 19.49 g. DI water, 0.31 g. isothiazolone
6-2. 0.10 g. sodium bromate, 19.59 g. DI water, 0.31 g. isothiazolone
6-3. 0.05 g. sodium bromate, 19.64 g. DI water, 0.31 g. isothiazolone
6-4. 0.20 g. sodium bromate, 19.49 g. pH 4.5 buffer, 0.31 g. isothiazolone
6-5. 0.10 g. sodium bromate, 19.59 g. pH 4.5 buffer, 0.31 g. isothiazolone All samples contain 1.5% isothiazolone and either 1%, 0.5%, or 0.25% sodium bromate. Samples 6-1, 6-2, and 6-3 were unbuffered (comparative). Samples were capped, shaken, and stored at 55° C. for 4 weeks. After storage, the samples were analyzed by HPLC with UV detection for percent isothiazolone remaining and for formation of brominated isothiazolones. The amount of brominated isothiazolones is reported in peak areas, as described in Example 5. These results are reported below.

| Sample | % Bromate | % MI/% CMI Remaining | Peak Area of Brominated Isothiazolone |
|---|---|---|---|
| 6-1* | 1.0 | 9/79 | 137,706 |
| 6-2* | 0.5 | 29/87 | 104,087 |
| 6-3* | 0.25 | 48/91 | 68,478 |
| 6-4 | 1.0 | 52/87 | 70,635 |
| 6-5 | 0.5 | 75/90 | 30,873 |

* = comparative

These data show that buffering of the sample is effective in reducing the formation of brominated isothiazolones at various concentrations of bromate stabilizer.

We claim:

1. Method of stabilizing 3-isothiazolone compound in an aqueous solution which is free of nitrate and nitrite stabilizer compounds comprising A) introducing sufficient bromate compound to stabilize said 3-isothiazolone, and B) buffering the pH of said solution in a range of 4 to 5.1.

2. Method according to claim 1 wherein said bromate compound is selected from the group consisting of sodium bromate, lithium bromate, potassium bromate, magnesium bromate, calcium bromate, strontium bromate, cobalt bromate, and zinc bromate.

3. Method according to claim 1 wherein said buffer is selected from the group consisting of acetate/acetic acid, citrate/citric acid, formate/formic acid, and butyrate/butyric acid.

4. Composition useful as a biocide comprising 3-isothiazolone compound, bromate compound present in an amount sufficient to stabilize said 3-isothiazolone against decomposition, solvent, and sufficient buffer to maintain the pH of said composition in a range of 4 to 5.1.

5. Composition according to claim 4 wherein said bromate compound is selected from the group consisting of sodium bromate, lithium bromate, potassium bromate, magnesium bromate, calcium bromate, strontium bromate, cobalt bromate, and zinc bromate.

6. Composition according to claim 4 wherein said 3-isothiazolone is one or more of 5-chloro-2-methyl-3-isothiazolone and 2-methyl-3-isothiazolone.

7. Composition according to claim 4 wherein said 3-isothiazolone compound(s) are present in a concentration of 0.5 to 5% by weight, based on said solution.

8. Composition according to claim 4 wherein said 3-isothiazolone is a mixture of 5-chloro-2-methyl-3-isothiazolone and 2-methyl-3-isothiazolone in a weight ratio of 3:1 to 4:1, said bromate is sodium bromate, said buffer is acetate/acetic acid, said solvent is water, weight percent of said 3-isothiazolone in said solution is 0.5 to 5%, and said pH is in the range of 4 to 5.1.

9. Method for inhibiting the growth of bacteria, fungi, yeast, or algae in a locus subject to contamination by bacteria, fungi, yeast, or algae which comprises incorporating into or onto said locus, in an amount which is effective to adversely affect the growth of bacteria, fungi, yeast, or algae, a composition according to claim 4.

10. Method of claim 9 wherein said locus is a cosmetic or a latex.

* * * * *